US012617887B2

(12) United States Patent
Suzuki et al.

(10) Patent No.: US 12,617,887 B2
(45) Date of Patent: May 5, 2026

(54) RESIN COMPOSITION FOR STEREOLITHOGRAPHY

(71) Applicant: KURARAY NORITAKE DENTAL INC., Kurashiki (JP)

(72) Inventors: Kenji Suzuki, Niigata (JP); Misaki Ito, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 784 days.

(21) Appl. No.: 17/798,358

(22) PCT Filed: Feb. 9, 2021

(86) PCT No.: PCT/JP2021/004832
§ 371 (c)(1),
(2) Date: Aug. 9, 2022

(87) PCT Pub. No.: WO2021/162007
PCT Pub. Date: Aug. 19, 2021

(65) Prior Publication Data

US 2023/0091071 A1 Mar. 23, 2023

(30) Foreign Application Priority Data

Feb. 10, 2020 (JP) ................................. 2020-020826

(51) Int. Cl.

| | |
|---|---|
| ***C08F 290/06*** | (2006.01) |
| ***A61K 6/887*** | (2020.01) |
| ***B33Y 70/00*** | (2020.01) |
| ***B33Y 80/00*** | (2015.01) |
| ***C08G 18/32*** | (2006.01) |
| ***C09D 4/00*** | (2006.01) |

(52) U.S. Cl.
CPC .......... *C08F 290/067* (2013.01); *A61K 6/887* (2020.01); *B33Y 70/00* (2014.12); *C08G 18/3206* (2013.01); *C09D 4/00* (2013.01); *B33Y 80/00* (2014.12)

(58) Field of Classification Search
CPC .............. C08F 290/067; C08F 222/104; C08F 220/343; C08F 222/102; A61K 6/887; A61K 6/62; B33Y 70/00; B33Y 10/00; C08G 18/3206; C09D 4/00; A61C 7/08; A61C 13/01; A61F 5/566
See application file for complete search history.

(56) References Cited

U.S. PATENT DOCUMENTS 5,247,038 A * 9/1993 Fukushima .............. G02B 1/04 526/321
2007/0081782 A1* 4/2007 Maeda .................. C08F 290/12 385/145
2014/0131908 A1* 5/2014 Sun .................... A61C 13/0013 264/16
2017/0224591 A1 8/2017 Vogel et al.
2019/0153249 A1 5/2019 Yang et al.
2021/0024682 A1 1/2021 Suzuki
2021/0340304 A1 11/2021 Ito et al.
(Continued)

FOREIGN PATENT DOCUMENTS

EP 3735957 A1 11/2020
EP 4083088 A1 11/2022
JP S56-144478 A 11/1981
(Continued)

OTHER PUBLICATIONS

International Search Report issued Apr. 13, 2021 in PCT/JP2021/004832 (with English translation), 6 pages.
(Continued)

*Primary Examiner* — Jessica M Roswell
(74) *Attorney, Agent, or Firm* — Element IP, PLC

(57) ABSTRACT

The present invention provides a resin composition for stereolithography that excels in strength, toughness, and water resistance in the form of a shaped article. The present invention relates to a resin composition for stereolithography that comprises a urethanized (meth)acrylic compound (A), a (meth)acrylate compound (B) containing no urethane bond, and a photopolymerization initiator (C), the compound (A) being a urethanized (meth)acrylic compound (A-1) having a polymer structure, and/or a urethanized (meth)acrylic compound (A-2) having no polymer structure, the compound (A-1) having a weight-average molecular weight of less than 1,000, the compound (A-2) having a molecular weight of less than 1,000, the compound (B) comprising at least one selected from the group consisting of a (meth)acrylate compound (b-I) represented by general formula (I), and a (meth)acrylate compound (b-II) represented by general formula (II).

(I)

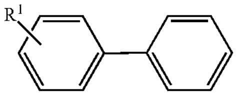

(II)

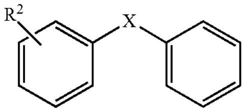

16 Claims, No Drawings

(56) References Cited

U.S. PATENT DOCUMENTS

| | | | |
|---|---|---|---|
| 2022/0153894 A1 | 5/2022 | Sakamaki et al. | |
| 2022/0218572 A1 | 7/2022 | Inoue et al. | |

FOREIGN PATENT DOCUMENTS

| | | | |
|---|---|---|---|
| JP | S60-247515 A | 12/1985 | |
| JP | 2000159621 A | 6/2000 | |
| JP | 2010189534 A | 9/2010 | |
| JP | 2017524020 A | 8/2017 | |
| JP | 2019001939 A | 1/2019 | |
| JP | 2019099750 A | 6/2019 | |
| JP | 2019534804 A | 12/2019 | |
| WO | WO-2012011434 A1 | 1/2012 | |
| WO | WO-2018181833 A1 | 10/2018 | |
| WO | WO-2019189566 A1 | 10/2019 | |
| WO | WO-2020071552 A1 | 4/2020 | |
| WO | WO-2020203981 A1 | 10/2020 | |
| WO | WO-2020218446 A1 | 10/2020 | |

OTHER PUBLICATIONS

Written Opinion issued Apr. 13, 2021 in PCT/JP2021/004832 (with English translation), 7 pages.

Extended European Search Report issued Jan. 24, 2024 in corresponding European Patent Application No. 21754607.6, 8 pages.

* cited by examiner

RESIN COMPOSITION FOR STEREOLITHOGRAPHY

TECHNICAL FIELD

The present invention relates to a resin composition for stereolithography. More specifically, the present invention relates to a resin composition for stereolithography that enables production of a three-dimensional shaped article having excellent strength, toughness, and water resistance. The resin composition of the present invention is particularly suited for denture base materials, dental occlusal splints, and appliances for the treatment of sleep apnea.

BACKGROUND ART

Patent Literature 1 discloses a photo-solidification technique, a method that produces a three-dimensional shaped article through a repeated procedure whereby a liquid photocurable resin composition is cured into a thin layer under controlled application of necessary amounts of light energy, and another layer of the photocurable resin composition is cured on the cured layer under controlled application of light after supplying another portion of the liquid photocurable resin composition onto the previously formed cured layer. Patent Literature 2 proposes a basic method for practical application of this technique, and, since its proposal, many other photo-solidification techniques have been proposed.

Vat stereolithography is a technique typically used for the optical fabrication of a three-dimensional shaped article. In this technique, a computer-controlled ultraviolet laser is selectively applied to draw a desired pattern on the surface of a liquid photocurable resin composition placed in a vat. By being cured, the resin forms a layer of a predetermined thickness, and another cured layer is continuously formed on the cured layer by applying an ultraviolet laser to the liquid photocurable resin composition supplied onto the previously cured layer in the amount necessary to form a single layer. The layering process is repeated to produce a three-dimensional shaped article of the desired shape. This technique has attracted great interest because it enables easy and precision production of the desired three-dimensional shaped article in a relatively short time period, even when the product has a very complex shape.

Three-dimensional shaped articles produced by stereolithography are used in an increasingly wider range of applications, from simple concept models to more complex models such as test models and prototypes. This has created a demand for higher shape precision in these three-dimensional shaped articles. In addition to satisfying such properties, these products are also required to have properties that are suited for their intended use. The field of dental materials is thought to greatly benefit from stereolithography because denture bases, dental occlusal splints, and appliances for the treatment of sleep apnea require shapes that vary from patient to patient, aside from being complex in shape.

Denture base materials are materials used for the gum as a part of a denture attached to replace missing teeth. The demand for dentures has rapidly increased in recent years because of increasing ageing populations.

Some dental splints are fitted to reposition the jaw while others are attached to teeth to reduce tooth wear due to clenching. There are also dental splints that are worn in the mouth to protect the stomatognathic system and the brain by reducing injuries caused when large external forces are applied to teeth and jawbones during sports activities in contact sports. In orthodontics, the use of dental splints has gained wide popularity over the last years because of aesthetics and detachability.

Among different types of appliances for the treatment of sleep apnea, of interest in the present invention are appliances (oral appliances, or OA) attached to teeth during sleep for the treatment of obstructive sleep apnea syndrome (OSAS). Such oral appliances have been increasingly used as appliances for the treatment of sleep apnea.

Common requirements for denture base materials, dental occlusal splints, and OA include strength, toughness, and water resistance. These are required particularly in what is commonly called non-clasp dentures, which are partial denture bases that do not have metal clasp parts. Low strength creates discomfort by increasing flexure or deformation during biting, whereas a loss of toughness necessitates frequent replacement as it increases susceptibility to breakage due to the impact of biting or deformation occurring upon installation. A loss of water resistance causes a reduction of mechanical properties during use, making the appliance practically useless by making the appliance easily deformable or breakable when it is installed.

Another consideration is that fabrication of denture base materials, dental occlusal splints, and appliances for the treatment of sleep apnea typically requires taking an impression of the oral cavity. This is seen as a problem because the procedure involves discomfort, and places a burden on patients, in addition to requiring high technical skills. Recent advances in digital technology have led to approaches that make use of an intraoral optical scan for taking an oral impression, and there have been attempts to apply stereolithography techniques for shaping. For fabrication, a resin composition for stereolithography is used. As a rule, resin compositions that develop strength tend to be more brittle, and attempts to impart toughness while maintaining strength often result in a flexible molecular structure, which encourages moisture penetration. In fact, it is difficult to satisfy all of strength, toughness, and water resistance.

Against this background, techniques are proposed that enable stereolithographic fabrication of a cured product having excellent toughness and water resistance. For example, Patent Literature 3 discloses a photocurable resin composition in which a urethanized (meth)acrylic compound has a specific oligomer backbone, and a specific mono(meth)acrylate compound has two aromatic rings are contained as essential components. However, because the resin composition of Patent Literature 3 is intended for flexible materials such as a mouthguard, the resin composition has low strength, and is not necessarily suited for applications such as denture bases.

CITATION LIST

Patent Literature

Patent Literature 1: JP S56-144478 A
Patent Literature 2: JP S60-247515 A
Patent Literature 3: WO2019/189566

SUMMARY OF INVENTION

Technical Problem

It is accordingly an object of the present invention to provide a resin composition for stereolithography that excels in strength, toughness, and water resistance. The present invention is particularly suited for denture base materials, dental occlusal splints, and appliances for the treatment of sleep apnea.

Solution to Problem

Specifically, the present invention includes the following.

[1] A resin composition for stereolithography, comprising:

a urethanized (meth)acrylic compound (A), a (meth) acrylate compound (B) containing no urethane bond, and a photopolymerization initiator (C), the urethanized (meth)acrylic compound (A) being a urethanized (meth)acrylic compound (A-1) having a polymer structure, and/or a urethanized (meth)acrylic compound (A-2) having no polymer structure, the urethanized (meth)acrylic compound (A-1) having a polymer structure having a weight-average molecular weight of less than 1,000, the urethanized (meth)acrylic compound (A-2) having no polymer structure having a molecular weight of less than 1,000, the (meth)acrylate compound (B) containing no urethane bond comprising at least one selected from the group consisting of a (meth)acrylate compound (b-I) represented by the following general formula (I), and a (meth)acrylate compound (b-II) represented by the following general formula (II),

[Chem. 1]

(I)

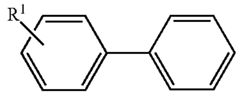

[Chem. 2]

(II)

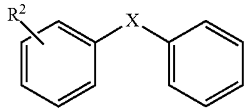

wherein $R^1$ and $R^2$ are each independently a group represented by the following general formula (i), or a group represented by the following general formula (ii), and X is a C1 to C6 divalent hydrocarbon group, or an oxygen atom,

[Chem. 3]

(i)

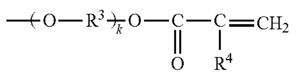

[Chem. 4]

(ii)

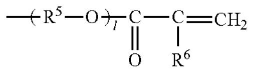

wherein $R^3$ and $R^5$ are each independently a C1 to C10 divalent hydrocarbon group, $R^4$ and $R^6$ are each independently a hydrogen atom or a methyl group, and k and l are each independently an integer of 0 to 6.

[2] The resin composition for stereolithography according to [1], wherein the number of the urethane bonds is three or fewer per molecule in the urethanized (meth)acrylic compound (A-1) having a polymer structure, and in the urethanized (meth)acrylic compound (A-2) having no polymer structure.

[3] The resin composition for stereolithography according to [1] or [2], wherein the urethanized (meth)acrylic compound (A) comprises the urethanized (meth)acrylic compound (A-2) having no polymer structure.

[4] The resin composition for stereolithography according to [3], wherein the urethanized (meth)acrylic compound (A-2) having no polymer structure comprises a (meth)acrylate compound.

[5] The resin composition for stereolithography according to any one of [1] to [4], wherein the urethanized (meth)acrylic compound (A-2) having no polymer structure comprises a polyfunctional (meth)acrylate compound.

[6] The resin composition for stereolithography according to any one of [1] to [5], wherein the urethanized (meth)acrylic compound (A) consists essentially of the compound (A-2) having no polymer structure.

[7] The resin composition for stereolithography according to any one of [1] to [6], wherein the urethanized (meth)acrylic compound (A-2) having no polymer structure comprises 2,2,4-trimethylhexamethylene bis(2-carbamoyloxyethyl)dimethacrylate, and/or N,N'-(2,2,4-trimethylhexamethylene) bis[2-(aminocarboxy)propane-1,3-diol]tetramethacrylate.

[8] The resin composition for stereolithography according to any one of [1] to [5], wherein the urethanized (meth)acrylic compound (A) comprises the urethanized (meth)acrylic compound (A-1) having a polymer structure.

[9] The resin composition for stereolithography according to [8], wherein the urethanized (meth)acrylic compound (A-1) having a polymer structure is a (meth)acrylate compound.

[10] The resin composition for stereolithography according to [8] or [9], wherein the content of the urethanized (meth) acrylic compound (A-1) having a polymer structure is in the range of 51 to 95 mass % in 100 mass % of polymerizable compounds.

[11] The resin composition for stereolithography according to any one of [1] to [10], wherein the polymer structure is a structure selected from the group consisting of a polyester, a polycarbonate, a polyurethane, a polyether, a poly-conjugated diene, and a hydrogenated poly-conjugated diene.

[12] The resin composition for stereolithography according to any one of [1] to [11], wherein k and l are each independently an integer of 1 to 4.

[13] The resin composition for stereolithography according to any one of [1] to [12], wherein the (meth)acrylate compound (B) containing no urethane bond comprises the (meth)acrylate compound (b-II), and X is an oxygen atom.

[14] The resin composition for stereolithography according to [13], wherein $R^2$ is a group represented by the general formula (ii).

[15] The resin composition for stereolithography according to any one of [1] to [14], wherein the (meth)acrylate compound (B) containing no urethane bond comprises the (meth)acrylate compound (b-I), and $R^1$ is a group represented by the general formula (i).

[16] The resin composition for stereolithography according to any one of [1] to [15], wherein the content of the photopolymerization initiator (C) is in the range of 0.01 to 20 parts by mass relative to total 100 parts by mass of the urethanized (meth)acrylic compound (A) and the (meth) acrylate compound (B) containing no urethane bond.

[17] The resin composition for stereolithography according to any one of [1] to [16], which further comprises a polymerization inhibitor (D), and the content of the polymerization inhibitor (D) is in the range of 0.1 to 100 parts by mass relative to 100 parts by mass of the photopolymerization initiator (C).

[18] The resin composition for stereolithography according to any one of [1] to [17], wherein a cured product of the resin composition for stereolithography has a flexural strength of 100 MPa or more, and a flexural modulus of 2.1 GPa or more.

[19] A dental material comprising a shaped article of a resin composition for stereolithography of any one of [1] to [18].

[20] A denture base material comprising a shaped article of a resin composition for stereolithography of any one of [1] to [18].

[21] A dental occlusal splint comprising a shaped article of a resin composition for stereolithography of any one of [1] to [18].

[22] A material for treating sleep disorder, comprising a shaped article of a resin composition for stereolithography of any one of [1] to [18].

[23] A method for stereolithographically producing a three-dimensional shaped article with a resin composition for stereolithography of any one of [1] to [18].

Advantageous Effects of Invention

A resin composition for stereolithography of the present invention excels in strength, toughness, and water resistance in the form of a shaped article. This makes a resin composition for stereolithography of the present invention suited for denture base materials and occlusal splints. A resin composition for stereolithography of the present invention can also be suitably used as a material of appliances for the treatment of sleep apnea.

DESCRIPTION OF EMBODIMENTS

A resin composition for stereolithography of the present invention comprises a urethanized (meth)acrylic compound (A), a (meth)acrylate compound (B) containing no urethane bond, and a photopolymerization initiator (C). In the present specification, the upper limits and lower limits of numeric ranges (for example, ranges of contents of components, ranges of values calculated from components, and numeric ranges of physical properties) can be combined appropriately. In the present specification, the numeric values represented by symbols in formulae can also be combined as appropriate.

Urethanized (Meth)Acrylic Compound (A)

In a resin composition for stereolithography of the present invention, the urethanized (meth)acrylic compound (A) is used to impart strength and fabricability to a shaped article of the resin composition for stereolithography. The urethanized (meth)acrylic compound (A) is a urethanized (meth) acrylic compound (A-1) having a polymer structure (hereinafter, also referred to simply as "compound (A-1) having a polymer structure"), and/or a urethanized (meth)acrylic compound (A-2) having no polymer structure (hereinafter, also referred to simply as "compound (A-2) having no polymer structure"). Owning to its polymer structure, the compound (A-1) having a polymer structure has a molecular weight distribution. The molecular weight distribution can be measured by gel permeation chromatography (GPC). In this specification, "polymer structure" means a structure with repeating monomer units with a degree of polymerization of two or more.

As an example, the urethanized (meth)acrylic compound (A) can be synthesized with ease by an addition reaction of an isocyanate group-containing compound having an alkylene backbone, a cycloalkylene backbone, or a phenylene backbone with a (meth)acrylic compound having a hydroxyl group (—OH). Another easy example is to react a polyol with a compound having a plurality of isocyanate groups, and causing the product to undergo an addition reaction with a (meth)acrylic compound having a hydroxyl group after introducing isocyanate groups to polyol terminals. In view of water resistance, it is however more preferable to directly react a compound having an isocyanate group with a (meth)acrylic compound having a hydroxyl group because the product, per molecule, has fewer urethane bonds, which are highly polar. In view of the superior strength, the compound (A-1) having a polymer structure needs to have a weight-average molecular weight (Mw) of less than 1,000. A softer object tends to result when the weight-average molecular weight is 1,000 or higher. In view of strength and water resistance, the weight-average molecular weight is preferably less than 950, more preferably less than 850. As used herein, "weight-average molecular weight" means a weight-average molecular weight in terms of polystyrene as determined by gel permeation chromatography (GPC). The notion of weight-average molecular weight does not apply to the urethanized (meth)acrylic compound (A) when it is a compound (A-2) having no polymer structure. In this case, it is required, in view of the superior strength, that the molecular weight, instead of a weight-average molecular weight, be less than 1,000. The shaped article tends to be softer when the molecular weight is 1,000 or more. In view of strength and water resistance, the molecular weight is preferably less than 750, more preferably less than 500. The molecular weight can be found by specifying the structure of the compound (A-2) having no polymer structure, and calculating the atomic weights of the constituent elements of the structure. The method used to specify the compound structure is not particularly limited, and known molecular-structure analysis methods can be used (including, for example, mass spectrometry; magnetic spectrometry such as nuclear magnetic resonance spectrometry; and X-ray crystallography).

Preferably, the urethanized (meth)acrylic compound (A) comprises a compound (A-2) having no polymer structure, such as a polyester, a polycarbonate, a polyurethane, or a polyether. When the urethanized (meth)acrylic compound (A) contains a polymer structure, flexibility increases, and water resistance tends to decrease as a result of an increased concentration of polar functional groups. However, the resin composition for stereolithography, even when the urethanized (meth)acrylic compound (A) comprises a compound (A-1) having a polymer structure, can reduce a concentration increase of polar functional groups, and can produce a shaped article having the desired strength and water resistance when, for example, the weight-average molecular weight of the compound (A-1) having a polymer structure is less than 1,000. In view of water resistance, the compound (A-1) having a polymer structure, and the compound (A-2) having no polymer structure each have preferably three or fewer of the urethane bonds, more preferably two or less of urethane bonds per molecule. The urethanized (meth)acrylic compound (A) may be used alone, or two or more thereof may be used in combination. A certain preferred embodiment (X-1) is, for example, a resin composition for stereolithography in which the urethanized (meth)acrylic compound (A) consists essentially of a compound (A-2) having no polymer structure, that is, the urethanized (meth)acrylic compound (A) is essentially free of a compound (A-1) having a polymer structure. A urethanized (meth)acrylic compound (A) consisting essentially of a compound (A-2) having no polymer structure means that the content of compound (A-1) having a polymer structure is less than 10.0 parts by mass, preferably less than 5.0 parts by mass, more preferably less than 1.0 part by mass, even more preferably less than 0.1 parts by mass, particularly preferably less than 0.01 parts by mass in total 100 parts by mass of the urethanized (meth)acrylic compound (A) present in the resin composition for stereolithography. Preferably, the compound (A-1) having a polymer structure is one containing no (meth)acrylamide group. Another preferred embodiment (X-2) is, for example, a resin composition for stereolithography in which the urethanized (meth)acrylic compound (A) comprises a compound (A-1) having a polymer structure, and the number of the urethane bonds is three or fewer per molecule in the urethanized (meth)acrylic compound (A-1). The number of urethane bonds can be controlled using a known method. In view of creating fewer urethane bonds per molecule, the number of urethane bonds can be adjusted by preferentially allowing a compound having an isocyanate group to directly react with a (meth)acrylic compound having a hydroxyl group in an addition reaction. For example, the urethanized (meth)acrylic compound (A-1) having a polymer structure, and the urethanized (meth) acrylic compound (A-2) having no polymer structure can have three or fewer of urethane bonds per molecule by using a reaction product of a diisocyanate (or a polyisocyanate having three isocyanate groups) and a (meth)acrylic compound having a hydroxyl group, or by using a reaction product of these compounds as a raw material. In this way, essentially three or fewer urethane bonds can be created per molecule in the urethanized (meth)acrylic compound (A-1) having a polymer structure, and in the urethanized (meth) acrylic compound (A-2) having no polymer structure.

Examples of the compound having an isocyanate group include methylene diisocyanate (MDI), hexamethylene diisocyanate (HDI), isophorone diisocyanate (IPDI), trimethylhexamethylene diisocyanate (TMHMDI), tricyclodecane diisocyanate (TCDDI), adamantane diisocyanate (ADI), tolylene diisocyanate (TDI), xylylene diisocyanate (XDI), and diphenylmethane diisocyanate (MDI), and polyisocyanates derived from these compounds and having three or more isocyanate groups. These may be used alone, or two or more thereof may be used in combination. In view of the superior strength and toughness of a shaped article of a resin composition for stereolithography of the present invention, preferred are HDI, IPDI, TMHMDI, and TCDDI, and more preferred are IPDI and TMHMDI.

Examples of the (meth)acrylic compound having a hydroxyl group include:

- hydroxy (meth)acrylate compounds such as 2-hydroxyethyl (meth)acrylate, 2-hydroxypropyl (meth)acrylate, 2-hydroxybutyl (meth)acrylate, 6-hydroxyhexyl (meth) acrylate, 10-hydroxydecyl (meth)acrylate, 3-chloro-2-hydroxypropyl (meth)acrylate, 2-hydroxy-3-phenoxypropyl (meth)acrylate, glycerin mono(meth)acrylate, 2-hydroxy-3-acryloyloxypropyl (meth)acrylate, 2,2-bis [4-[3-(meth)acryloyloxy-2-hydroxypropoxy]phenyl] propane, 1,2-bis[3-(meth)acryloyloxy-2-hydroxypropoxy]ethane, pentaerythritol tri(meth)acrylate, and tri or tetra(meth)acrylates of dipentaerythritol; and
- hydroxy(meth)acrylamide compounds such as N-hydroxyethyl(meth)acrylamide, and N,N-bis(2-hydroxyethyl)(meth)acrylamide.

These may be used alone, or two or more thereof may be used in combination. In view of superior toughness of a shaped article of a resin composition for stereolithography of the present invention, 2-hydroxyethyl (meth)acrylate, 2-hydroxypropyl (meth)acrylate, 2-hydroxy-3-acryloyloxypropyl (meth)acrylate, and N-hydroxyethyl(meth)acrylamide are preferred, and 2-hydroxyethyl (meth)acrylate is more preferred.

The addition reaction of a compound having an isocyanate group, and a (meth)acrylic compound having a hydroxyl group may follow a known method, and is not particularly limited.

Preferably, the compound (A-1) having a polymer structure has a polymer structure and a urethane bond, wherein the polymer structure is one selected from the group consisting of a polyester, a polycarbonate, a polyurethane, a polyether, a poly-conjugated diene, and a hydrogenated poly-conjugated diene. More preferably, the compound (A-1) having a polymer structure is a (meth)acrylate compound having such a polymer structure and a urethane bond.

The compound (A-1) having a polymer structure can be synthesized with ease by an addition reaction of a polyol containing a polymer structure selected from the group consisting of a polyester, a polycarbonate, a polyurethane, a polyether, a poly-conjugated diene, and a hydrogenated poly-conjugated diene; a compound having an isocyanate group; and a (meth)acrylate compound having a hydroxyl group. Examples of the polyester structure include: a polymer of a dicarboxylic acid (e.g., an aromatic dicarboxylic acid such as phthalic acid or isophthalic acid, or an unsaturated aliphatic dicarboxylic acid such as maleic acid) and an aliphatic diol having 2 to 18 carbon atoms; a polymer of a dicarboxylic acid (e.g., a saturated aliphatic dicarboxylic acid such as adipic acid or sebacic acid) and an aliphatic glycol having 2 to 18 carbon atoms; a β-propiolactone polymer; a γ-butyrolactone polymer; a δ-valerolactone polymer; an ε-caprolactone polymer; and a copolymer of these. Preferred are a polymer of a dicarboxylic acid (an aromatic dicarboxylic acid such as phthalic acid or isophthalic acid, or an unsaturated aliphatic dicarboxylic acid such as maleic acid) and an aliphatic diol having 2 to 12 carbon atoms; and a polymer of a dicarboxylic acid (a saturated aliphatic dicarboxylic acid such as adipic acid or sebacic acid) and an aliphatic glycol having 2 to 12 carbon atoms. Examples of the polycarbonate include a polycarbonate derived from an aliphatic diol having 2 to 18 carbon atoms, a polycarbonate derived from bisphenol A, and a polycarbonate derived from a C2 to C18 aliphatic diol and bisphenol A. Preferred are a polycarbonate derived from an aliphatic diol having 2 to 12 carbon atoms, a polycarbonate derived from bisphenol A, and a polycarbonate derived from a C2 to C12 aliphatic diol and bisphenol A. Examples of the polyurethane include a polymer of a C2 to C18 aliphatic diol and a C1 to C18 diisocyanate. Preferred is a polymer of a C2 to C12 aliphatic diol and a C1 to C12 diisocyanate. Examples of the polyether include polyethylene glycol, polypropylene glycol, polybutylene glycol, and poly(1-methylbutylene glycol). Examples of the poly-conjugated diene and hydrogenated poly-conjugated diene include 1,4-polybutadiene, 1,2-polybutadiene, polyisoprene, poly(butadiene-isoprene), poly(butadiene-styrene), poly(isoprene-styrene), polyfarnesene, and hydrogenated products of these. Among these structures, polyester is preferred in view of superior toughness. In view of superior water resistance and toughness, it is preferable that the polyester structure contain a polyol moiety having a structure derived from a C4 to C18 aliphatic diol unit having a branched structure; and an isophthalic acid ester or a sebacic acid ester. In view of superior water resistance and fabricability, it is more preferable that the polyester structure contain a polyol moiety having a structure derived from a C4 to C12 aliphatic diol unit having a branched structure; and an isophthalic acid ester or a sebacic acid ester. Even more preferably, the polyester structure contains a polyol moiety having a structure derived from a C5 to C12 aliphatic diol unit having a branched structure; and an isophthalic acid ester or a sebacic acid ester. A polyol having these polymer structures can be used for the production of compound (A-1) having a polymer structure. In view of the superior strength and water resistance, preferred are polyester, polycarbonate, and poly-conjugated diene structures. A polyol having these polymer structures can be used for the production of compound (A-1) having a polymer structure.

Examples of the C4 to C18 aliphatic diol unit having a branched structure include 2-methyl-1,3-propanediol, 2,2-diethyl-1,3-propanediol, 1,3-butanediol, 2-methyl-1,4-butanediol, neopentyl glycol, 3-methyl-1,5-pentanediol, 2-methyl-1,8-octanediol, 2,7-dimethyl-1,8-octanediol, 2-methyl-1,9-nonanediol, 2,8-dimethyl-1,9-nonanediol, 2-methyl-1,10-decanediol, 2,9-dimethyl-1,10-decanediol, 2-methyl-1,11-undecanediol, 2,10-dimethyl-1,11-undecanediol, 2-methyl-1,12-dodecanediol, 2,11-dimethyl-1,12-dodecanediol, 2-methyl-1,13-tridecanediol, 2,12-dimethyl-1,13-tridecanediol, 2-methyl-1,14-tetradecanediol, 2,13-dimethyl-1,14-tetradecanediol, 2-methyl-1,15-pentadecanediol, 2,14-dimethyl-1,15-pentadecanediol, 2-methyl-1,16-hexadecanediol, and 2,15-dimethyl-1,16-hexadecanediol. In view of providing a resin composition for stereolithography having superior curability and low viscosity, the polyol components used are preferably C5 to C12 aliphatic diols having a methyl-group side chain, for example, such as 2-methyl-1,4-butanediol, 3-methyl-1,5-pentanediol, 2-methyl-1,8-octanediol, 2,7-dimethyl-1,8-octanediol, 2-methyl-1,9-nonanediol, and 2,8-dimethyl-1,9-nonanediol. The polyol components are more preferably 2-methyl-1,4-butanediol, 3-methyl-1,5-pentanediol, 2-methyl-1,8-octanediol, and 2,7-dimethyl-1,8-octanediol, even more preferably 3-methyl-1,5-pentanediol, and 2-methyl-1,8-octanediol.

The compound (A-1) having a polymer structure is, for example, a reaction product of any combination of: a polyol having at least one polymer structure selected from the group consisting of a polyester, a polycarbonate, a polyurethane, a polyether, a poly-conjugated diene, and a hydrogenated poly-conjugated diene; a compound having an isocyanate group; and a (meth)acrylic compound having a hydroxyl group. The reaction product is preferably a (meth) acrylate compound. The compound (A-1) having a polymer structure may be used alone, or two or more thereof may be used in combination. A certain embodiment (X-3) is, for example, a resin composition for stereolithography in which the compound (A-1) having a polymer structure does not contain a (meth)acrylamide oligomer.

Examples of the compound (A-2) having no polymer structure include (meth)acrylate compounds, for example, bifunctional (meth)acrylates such as 2,2,4-trimethylhexamethylene bis(2-carbamoyloxyethyl)dimethacrylate (commonly known as U DMA), 2,4-tolylene bis(2-carbamoyloxyethyl)dimethacrylate, bishydroxyethyl methacrylate-isophorone diurethane, 2,4-tolylene bis(2-carbamoyloxyethyl)dimethacrylate, and hexamethylene bis{2-carbamoyloxy-3-phenoxypropyl}diacrylate; and tri and higher functional (meth)acrylates such as N,N'-(2,2,4-trimethylhexamethylene) bis[2-(aminocarboxy)propane-1,3-diol]tetramethacrylate, and 2,4-tolylene bis(2-carbamoyloxyethyl)hexaacrylate. These may be used alone, or two or more thereof may be used in combination. In view of strength and toughness, 2,2,4-trimethylhexamethylene bis(2-carbamoyloxyethyl)dimethacrylate, and N, N'-(2,2,4-trimethylhexamethylene) bis[2-(aminocarboxy)propane-1,3-diol]tetramethacrylate are preferred, and 2,2,4-trimethylhexamethylene bis(2-carbamoyloxyethyl) dimethacrylate is more preferred.

The content of the urethanized (meth)acrylic compound (A) (a total content when the urethanized (meth)acrylic compound (A) comprises both the compound (A-1) having a polymer structure, and the compound (A-2) having no polymer structure) in a resin composition for stereolithography of the present invention is preferably 10 to 99 parts by mass in total 100 parts by mass of the urethanized (meth) acrylic compound (A) and the (meth)acrylate compound (B) containing no urethane bond (hereinafter, a total of urethanized (meth)acrylic compound (A) and (meth)acrylate compound (B) containing no urethane bond also will be referred to simply as "total"). In view of even superior fabricability and even superior strength of the shaped article, the content of the urethanized (meth)acrylic compound (A) is more preferably 30 to 90 parts by mass, even more preferably 50 to 80 parts by mass. In a certain preferred embodiment (X-4), the urethanized (meth)acrylic compound (A) contained in the resin composition for stereolithography comprises a compound (A-2) having no polymer structure, and the content of the compound (A-2) having no polymer structure is preferably 10 to 99 parts by mass in total 100 parts by mass of urethanized (meth)acrylic compound (A) and (meth)acrylate compound (B) containing no urethane bond. In view of even superior fabricability and even superior strength of the shaped article, the content of compound (A-2) having no polymer structure is more preferably 30 to 90 parts by mass, even more preferably 50 to 80 parts by mass. In another certain preferred embodiment (X-5), the urethanized (meth)acrylic compound (A) contained in the resin composition for stereolithography comprises a compound (A-1) having a polymer structure, and the content of the compound (A-1) having a polymer structure is preferably 51 to 95 parts by mass in total 100 parts by mass of urethanized (meth)acrylic compound (A) and (meth)acrylate compound (B) containing no urethane bond. In view of even superior fabricability and even superior strength of the shaped article, the content of compound (A-1) having a polymer structure is more preferably 55 to 90 parts by mass, even more preferably 60 to 85 parts by mass in total 100 parts by mass of urethanized (meth)acrylic compound (A) and (meth)acrylate compound (B) containing no urethane bond. In the preferred embodiment (X-5), the content of compound (A-1) having a polymer structure is preferably 51 to 95 mass % in 100 mass % of polymerizable compounds. In view of even superior fabricability and even superior strength of the shaped article, the content of compound (A-1) having a polymer structure is more preferably 55 to 90 mass %, even more preferably 60 to 85 mass % in 100 mass % of polymerizable compounds. Here, "100 mass % of polymerizable compounds" means total 100 mass % of urethanized (meth)acrylic compound (A), (meth)acrylate compound (B) containing no urethane bond, and (meth) acrylamide compound (D) when the resin composition for stereolithography comprises a (meth)acrylamide compound (D). In another preferred embodiment (X-6), the content of the compound (A-1) having a polymer structure present in the resin composition for stereolithography is preferably 51 to 95 mass % of the total of the resin composition for stereolithography. In view of even superior toughness, the content of the compound (A-1) having a polymer structure is more preferably 55 to 90 mass %, even more preferably 60 to 85 mass %.

(Meth)Acrylate Compound (B) Containing No Urethane Bond

In a resin composition for stereolithography of the present invention, the (meth)acrylate compound (B) containing no urethane bond can reduce the viscosity of the resin composition for stereolithography, and is used to impart toughness and water resistance to the shaped article. The (meth) acrylate compound (B) containing no urethane bond may be used alone, or two or more thereof may be used in combination.

The (meth)acrylate compound (B) containing no urethane bond comprises at least one selected from the group consisting of a (meth)acrylate compound (b-I) represented by the general formula (I) above (hereinafter, referred to as "(meth)acrylate compound (b-I)"), and a (meth)acrylate compound (b-II) represented by the general formula (II) above (hereinafter, referred to as "(meth)acrylate compound (b-II)"). The following describes the (meth)acrylate compound (b-I) and the (meth)acrylate compound (b-II).

The symbols used in formula (I) are as follows. In formula (I), $R^1$ is a group represented by the general formula (i), or a group represented by general formula (ii). In view of providing superior curability to a resin composition for stereolithography of the present invention, $R^4$ and $R^6$ in formula (i) or (ii) are each independently a hydrogen atom or a methyl group. Preferred for superior fabricability of the resin composition for stereolithography and superior toughness of the cured product is a hydrogen atom. $R^3$ and $R^5$ are each independently a C1 to C10 divalent hydrocarbon group. In view of reducing the viscosity of the resin composition for stereolithography and providing superior fabricability, the hydrocarbon group has preferably 1 to 6 carbon atoms, more preferably 1 to 4 carbon atoms, even more preferably 1 to 3 carbon atoms. Examples of the hydrocarbon group include a linear or branched alkylene group having 1 to 10 carbon atoms; a divalent cycloalkylene group having 3 to 10 carbon atoms; and a phenylene group. k and l are each independently an integer of 0 to 6. In view of reducing the viscosity of the resin composition for stereolithography and providing superior fabricability, k is preferably 1 to 4, more preferably 1 to 3, even more preferably 1 to 2, particularly preferably 1. Preferably, l is 1 to 4, more preferably 1 to 2, even more preferably 1.

Examples of the (meth)acrylate compound (b-I) include o-phenylphenol (meth)acrylate, m-phenylphenol (meth) acrylate, p-phenylphenol (meth)acrylate, methoxylated-o-phenylphenol (meth)acrylate, methoxylated-m-phenylphenol (meth)acrylate, methoxylated-p-phenylphenol (meth) acrylate, ethoxylated-o-phenylphenol (meth)acrylate, ethoxylated-m-phenylphenol (meth)acrylate, ethoxylated-p-phenylphenol (meth)acrylate, propoxylated-o-phenylphenol (meth)acrylate, propoxylated-m-phenylphenol (meth)acrylate, propoxylated-p-phenylphenol (meth)acrylate, butoxylated-o-phenylphenol (meth)acrylate, butoxylated-m-phenylphenol (meth)acrylate, and butoxylated-p-phenylphenol (meth)acrylate. These may be used alone, or two or more thereof may be used in combination. In view of superior fabricability of the resin composition for stereolithography and superior toughness and water resistance of the cured product, more preferred are ethoxylated-o-phenylphenol acrylate, ethoxylated-m-phenylphenol acrylate, ethoxylated-p-phenylphenol acrylate, propoxylated-o-phenylphenol acrylate, propoxylated-m-phenylphenol acrylate, and propoxylated-p-phenylphenol acrylate, even more preferred are ethoxylated-o-phenylphenol acrylate, ethoxylated-m-phenylphenol acrylate, and ethoxylated-p-phenylphenol acrylate, particularly preferred are ethoxylated-o-phenylphenol acrylate, and ethoxylated-m-phenylphenol acrylate, most preferred is ethoxylated-o-phenylphenol acrylate.

The symbols used in formula (II) are as follows. In formula (II), X is a C1 to C6 divalent hydrocarbon group or an oxygen atom. An oxygen atom is preferred in view of reducing the viscosity of the resin composition for stereolithography and providing superior fabricability. $R^2$ is a group selected from the general formula (i) or (ii). In view of providing superior curability to a resin composition for stereolithography of the present invention, $R^4$ and $R^6$ in formula (i) or (ii) are each independently a hydrogen atom or a methyl group. A hydrogen atom is preferred in view of superior curability of the resin composition for stereolithography and superior flexibility of the cured product. $R^3$ and $R^5$ are each independently a C1 to C10 divalent hydrocarbon group. In view of reducing the viscosity of the resin composition for stereolithography and providing superior curability, the hydrocarbon group has preferably 1 to 6 carbon atoms, more preferably 1 to 4 carbon atoms, even more preferably 1 to 3 carbon atoms. Examples of the hydrocarbon group include a linear or branched alkylene group having 1 to 10 carbon atoms; a divalent cycloalkylene group having 3 to 10 carbon atoms; and a phenylene group. k and l are each independently an integer of 0 to 6. In view of reducing the viscosity of the resin composition for stereolithography and providing superior fabricability, k is preferably 1 to 4, more preferably 1 to 3, even more preferably 1 to 2, particularly preferably 1. Preferably, l is 1 to 4, more preferably 1 to 2, even more preferably 1.

Examples of the (meth)acrylate compound (b-II) include o-phenoxybenzyl (meth)acrylate, m-phenoxybenzyl (meth) acrylate, p-phenoxybenzyl (meth)acrylate, 2-(o-phenoxyphenyl)ethyl (meth)acrylate, 2-(m-phenoxyphenyl)ethyl (meth)acrylate, 2-(p-phenoxyphenyl)ethyl (meth)acrylate, 3-(o-phenoxyphenyl)propyl (meth)acrylate, 3-(m-phenoxyphenyl)propyl (meth)acrylate, 3-(p-phenoxyphenyl)propyl (meth)acrylate, 4-(o-phenoxyphenyl)butyl (meth)acrylate, 4-(m-phenoxyphenyl)butyl (meth)acrylate, 4-(p-phenoxyphenyl)butyl (meth)acrylate, 5-(o-phenoxyphenyl)pentyl (meth)acrylate, 5-(m-phenoxyphenyl)pentyl (meth)acrylate, 5-(p-phenoxyphenyl)pentyl (meth)acrylate, 6-(o-phenoxyphenyl)hexyl (meth)acrylate, 6-(m-phenoxyphenyl)hexyl (meth)acrylate, and 6-(p-phenoxyphenyl)hexyl (meth)acrylate. These may be used alone, or two or more thereof may be used in combination. In view of superior fabricability of the resin composition for stereolithography and superior toughness and water resistance of the shaped article, more preferred are o-phenoxybenzyl acrylate, m-phenoxybenzyl acrylate, p-phenoxybenzyl acrylate, 2-(o-phenoxyphenyl) ethyl acrylate, 2-(m-phenoxyphenyl)ethyl acrylate, and 2-(p-phenoxyphenyl)ethyl acrylate, even more preferred are o-phenoxybenzyl acrylate, m-phenoxybenzyl acrylate, and p-phenoxybenzyl acrylate, particularly preferred are o-phenoxybenzyl acrylate, and m-phenoxybenzyl acrylate, most preferred is m-phenoxybenzyl acrylate.

The content of the (meth)acrylate compound (B) containing no urethane bond in a resin composition for stereolithography of the present invention is preferably 1 to 90 parts by mass in total 100 parts by mass of the urethanized (meth) acrylic compound (A) and the (meth)acrylic acid ester (B) containing no urethane bond. In view of even superior fabricability and even superior toughness and water resistance of the shaped article, the content of (meth)acrylate compound (B) containing no urethane bond is more preferably 10 to 70 parts by mass, even more preferably 20 to 50 parts by mass. In another certain preferred embodiment (X-7), the urethanized (meth)acrylic compound (A) contained in the resin composition for stereolithography of embodiment (X-5) or (X-6) comprises a compound (A-1) having a polymer structure, and the content of (meth) acrylate compound (B) containing no urethane bond is preferably 5 to 49 parts by mass in total 100 parts by mass of urethanized (meth)acrylic compound (A) and (meth) acrylate compound (B) containing no urethane bond. In view of even superior fabricability and even superior toughness and water resistance of the shaped article, the content of (meth)acrylate compound (B) containing no urethane bond is more preferably 10 to 45 parts by mass, even more preferably 15 to 40 parts by mass. In the preferred embodiment (X-7), the content of (meth)acrylate compound (B) containing no urethane bond is preferably 5 to 49 mass % in total 100 mass % of polymerizable compounds. In view of even superior fabricability and even superior toughness and water resistance of the shaped article, the content of (meth) acrylate compound (B) containing no urethane bond is more preferably 10 to 45 mass %, even more preferably 15 to 40 mass %.

The polymerizable compounds contained in a resin composition for stereolithography of the present invention may consist essentially of the urethanized (meth)acrylic compound (A) and the (meth)acrylate compound (B) containing no urethane bond. Polymerizable compounds being consisting essentially of the urethanized (meth)acrylic compound (A) and the (meth)acrylate compound (B) containing no urethane bond means that the content of polymerizable compounds other than the urethanized (meth)acrylic compound (A) and the (meth)acrylate compound (B) containing no urethane bond (for example, a compound having an ethylenic unsaturated group, such as a (meth)acrylamide urethane oligomer) is less than 10.0 parts by mass, preferably less than 5.0 parts by mass, more preferably less than 1.0 part by mass, even more preferably less than 0.1 parts by mass, particularly preferably less than 0.01 parts by mass in total 100 parts by mass of the polymerizable compounds present in the resin composition for stereolithography.

Photopolymerization Initiator (C)

The photopolymerization initiator (C) used in the present invention may be selected from polymerization initiators used in industry, preferably from photopolymerization initiators used in dentistry.

Examples of the photopolymerization initiator (C) include (bis)acylphosphine oxides, thioxanthones or quaternary ammonium salts of thioxanthones, ketals, α-diketones, coumarins, anthraquinones, benzoin alkyl ether compounds, and α-aminoketone compounds. The photopolymerization initiator (C) may be used alone, or two or more thereof may be used in combination.

Preferably, the photopolymerization initiator (C) is at least one selected from the group consisting of (bis)acylphosphine oxides and α-diketones. In this way, a resin composition for stereolithography can be obtained that has excellent photocurability both in the ultraviolet and visible regions, and that shows sufficient photocurability even when the light source is a laser, a halogen lamp, a light emitting diode (LED), or a xenon lamp.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoyldiphenylphosphine oxide. Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Other examples include compounds mentioned in JP 2000-159621 A.

Among these (bis)acylphosphine oxides, particularly preferred as photopolymerization initiator (C) are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Camphorquinone is particularly preferred when the light source used is a visible light source.

The content of the photopolymerization initiator (C) in a resin composition for stereolithography of the present invention is not particularly limited. However, in view of curability and other properties of the resin composition for stereolithography, the content of photopolymerization initiator (C) is preferably 0.01 to 20 parts by mass relative to total 100 parts by mass of urethanized (meth)acrylic compound (A) and (meth)acrylate compound (B) containing no urethane bond. When the content of photopolymerization initiator (C) is less than 0.01 parts by mass, polymerization may not sufficiently proceed to form a formed product. The content of photopolymerization initiator (C) is more preferably 0.05 or more parts by mass, even more preferably 0.1 parts or more by mass, particularly preferably 0.5 parts or more by mass, most preferably 1.5 parts or more by mass relative to total 100 parts by mass of urethanized (meth)acrylic compound (A) and (meth)acrylate compound (B) containing no urethane bond. When the content of photopolymerization initiator (C) is more than 20 parts by mass, the photopolymerization initiator (C) may precipitate out of the resin composition for stereolithography when the solubility of the photopolymerization initiator itself is low. The content of photopolymerization initiator (C) is more preferably 15 parts or less by mass, even more preferably 10 parts or less by mass, particularly preferably 5.0 parts or less by mass, most preferably 3.0 parts or less by mass relative to total 100 parts by mass of urethanized (meth)acrylic compound (A) and (meth)acrylate compound (B) containing no urethane bond.

A resin composition for stereolithography of the present invention is not particularly limited, as long as it comprises the urethanized (meth)acrylic compound (A), the (meth) acrylate compound (B) containing no urethane bond, and the photopolymerization initiator (C). For example, a resin composition for stereolithography of the present invention may comprise components other than these. As an example, a resin composition for stereolithography of the present invention may comprise a (meth)acrylamide compound (D). The (meth)acrylamide compound (D) is not particularly limited, as long as it has a (meth)acrylamide skeleton.

Examples of the (meth)acrylamide compound (D) include monofunctional (meth)acrylamide compounds such as N,N-dimethyl(meth)acrylamide, N,N-diethyl(meth)acrylamide, N,N-di-n-propyl(meth)acrylamide, N-isopropyl(meth)acrylamide, N,N-di-n-butyl(meth)acrylamide, N,N-di-n-hexyl (meth)acrylamide, N,N-di-n-octyl(meth)acrylamide, N,N-di-2-ethylhexyl(meth)acrylamide, N-(2-hydroxyethyl) (meth)acrylamide, N,N-bis(2-hydroxyethyl)(meth) acrylamide, N-acryloylmorpholine, N,N-dimethylaminoethyl(meth)acrylamide, N,N-diethylaminoethyl(meth)acrylamide, N,N-dipropylaminoethyl(meth)acrylamide, N,N-dibutylaminoethyl(meth)acrylamide, N,N-dimethylaminopropyl(meth)acrylamide, N,N-diethylaminopropyl(meth)acrylamide, N,N-dipropylaminopropyl(meth)acrylamide, N,N-dibutylaminopropyl(meth)acrylamide, N,N-dimethylaminobutyl(meth)acrylamide, N,N-diethylaminobutyl(meth)acrylamide, N,N-dipropylaminobutyl(meth)acrylamide, and N,N-dibutylaminobutyl(meth)acrylamide. These may be used alone, or two or more thereof may be used in combination. A certain preferred embodiment (X-8) is, for example, a resin composition for stereolithography that does not comprise a (meth)acrylamide compound (D) in any of the embodiments (X-1) to (X-7). A resin composition for stereolithography of the present invention may be produced according to a known method.

A resin composition for stereolithography of the present invention may comprise a polymerization accelerator to improve photocurability, provided that addition of a polymerization accelerator is not detrimental to the intent and purpose of the present invention. Examples of the polymerization accelerator include ethyl 4-(N,N-dimethylamino) benzoate, methyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino)benzophenone, and butyl 4-(N,N-dimethylamino)benzoate. These may be used alone, or two or more thereof may be used in combination. In view of imparting superior curability to the resin composition for stereolithography, preferred is at least one selected from the group consisting of ethyl 4-(N,N-dimethylamino)benzoate, n-butoxyethyl 4-(N,N-dimethylamino)benzoate, and 4-(N,N-dimethylamino)benzophenone.

The resin composition for stereolithography of the present invention may further comprise a filler mixed therein to adjust paste properties or to improve the mechanical strength of a shaped article of the resin composition for stereolithography. Examples of the filler include organic fillers, inorganic fillers, and organic-inorganic composite fillers. The filler may be used alone, or two or more thereof may be used in combination.

Examples of the organic fillers include polymethyl methacrylate, polyethyl methacrylate, a methyl methacrylate-ethyl methacrylate copolymer, crosslinked polymethyl methacrylate, crosslinked polyethyl methacrylate, polyesters, polyamides, polycarbonates, polyphenylene ethers, polyoxymethylene, polyvinyl chloride, polystyrene, polyethylene, polypropylene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone, or two or more thereof may be used in combination. The organic filler is not limited to a particular shape, and may be appropriately selected from organic fillers of different particle diameters.

Examples of the materials of the inorganic fillers include quartz, silica, alumina, silica-titania, silica-titania-barium oxide, silica-zirconia, silica-alumina, lanthanum glass, borosilicate glass, soda glass, barium glass, strontium glass, glass-ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone, or two or more thereof may be used in combination. The inorganic filler is not limited to a particular shape, and may be appropriately selected from inorganic fillers of different shapes, such as irregularly shaped fillers, and spherical fillers.

A resin composition for stereolithography of the present invention may comprise a polymer to alter properties such as flexibility and flowability, provided that addition of a polymer is not detrimental to the intent and purpose of the present invention. Examples of polymers that may be added in the present invention include natural rubber, synthetic polyisoprene rubber, liquid polyisoprene rubber and hydrogenated products thereof, polybutadiene rubber, liquid polybutadiene rubber and hydrogenated products thereof, styrene-butadiene rubber, chloroprene rubber, ethylene-propylene rubber, acryl rubber, isoprene-isobutylene rubber, acrylonitrile-butadiene rubber, and styrene elastomers. Specific examples of other polymers that may be added in the present invention include a polystyrene-polyisoprene-polystyrene block copolymer, a polystyrene-polybutadiene-polystyrene block copolymer, a poly(a-m ethylstyrene)-polybutadiene-poly(a-methylstyrene) block copolymer, a poly(p-methylstyrene)-polybutadiene-poly(p-methylstyrene) block copolymer, and hydrogenated products of these.

A resin composition for stereolithography of the present invention may optionally comprise a softener. Examples of the softener include petroleum-based softeners such as paraffinic, naphthenic, and aromatic process oils, and vegetable oil-base softeners such as paraffin, peanut oil, and rosin. These softeners may be used alone, or two or more thereof may be used in combination. The softener content is not particularly limited, provided that it is not detrimental to the intent and purpose of the present invention. Typically, the softener content is 200 parts or less by mass, preferably 100 parts or less by mass relative to total 100 parts by mass of urethanized (meth)acrylic compound (A) and (meth)acrylate compound (B) containing no urethane bond.

A resin composition for stereolithography of the present invention may comprise a known stabilizer, in order to inhibit property deterioration or adjust photocurability, or to improve strength and elastic modulus. Examples of such stabilizers include a polymerization inhibitor (D), ultraviolet absorbers, and antioxidants. The stabilizer may be used alone, or two or more thereof may be used in combination.

Examples of the polymerization inhibitor (D) include hydroquinone, hydroquinone monomethyl ether, dibutylhydroquinone, dibutylhydroquinone monomethyl ether, 4-t-butyl catechol, 2-t-butyl-4,6-dimethylphenol, 2,6-di-t-butylphenol, and 3,5-di-t-butyl-4-hydroxytoluene. In view of curability and the effect to inhibit property deterioration, the content of polymerization inhibitor (D) is preferably 0.001 to 5.0 parts by mass, more preferably 0.05 to 2.5 parts by mass, even more preferably 0.1 to 1.0 parts by mass relative to total 100 parts by mass of urethanized (meth) acrylic compound (A) and (meth)acrylate compound (B) containing no urethane bond. In view of the effect to improve strength and elastic modulus, the content of polymerization inhibitor (D) is preferably 0.1 to 100 parts by mass, more preferably 1.0 to 60 parts by mass, even more preferably 10 to 40 parts by mass relative to 100 parts by mass of photopolymerization initiator (C).

A resin composition for stereolithography of the present invention may comprise a known additive, in order to adjust shades or paste properties. Examples of such additives include pigments, dyes, solvents (e.g., organic solvents), and thickeners. The additive may be used alone, or two or more thereof may be used in combination.

A resin composition for stereolithography of the present invention excels in strength, toughness, and water resistance in the form of a shaped article, in addition to having excellent fabricability. This makes a resin composition for stereolithography of the present invention usable in applications where such advantages can be exploited. Specifically, a resin composition for stereolithography of the present invention can be most suitably used for denture base materials, occlusal splints, and appliances for the treatment of sleep apnea. A shaped article of a resin composition for stereolithography of the present invention may have a shape that depends on intended use. In a resin composition for stereolithography of the present invention, the type and content of each component (urethanized (meth)acrylic compound (A), (meth)acrylate compound (B) containing no urethane bond, polymerization initiator (C), and optional components such as (meth)acrylamide compound (D), a polymerization accelerator, a filler, a polymer, a softener, a stabilizer, and an additive) may be optionally adjusted for different uses, for example, denture base materials, occlusal splints, and appliances for the treatment of sleep apnea.

A cured product of a resin composition for stereolithography of the present invention has a flexural modulus ranging preferably from 2.1 to 4.0 GPa, more preferably from 2.5 to 3.5 GPa, even more preferably from 2.75 to 3.25 GPa. A cured product of a resin composition for stereolithography of the present invention has a flexural strength (three-point flexural strength) of preferably 80 MPa or more, more preferably 90 MPa or more, even more preferably 100 MPa or more, particularly preferably 120 MPa or more. The methods of measurement of flexural modulus and flexural strength are as described in the EXAMPLES section below. In view of strength and toughness, a cured product of a resin composition for stereolithography of the present invention has an A hardness (type A durometer hardness) at 23° C. of preferably 86 or more, more preferably 90 or more, even more preferably 95 or more as measured for a specimen (shaped article) measuring 2 mm in thickness, 11 cm in length, and 5 cm in width using a type A durometer (Asker rubber hardness meter, A Type; Kobunshi Keiki Co., Ltd.) according to JIS K 7215:1986. More preferably, a cured product of a resin composition for stereolithography of the present invention has a D hardness at 23° C. of 40 to 95, even more preferably 50 to 90 when a specimen of the same dimensions is measured for hardness (D hardness) at 23° C. using a type D durometer (Asker rubber hardness meter, D Type; Kobunshi Keiki Co., Ltd.) according to JIS K 7215:1986.

A resin composition for stereolithography of the present invention can be used in a wide variety of applications by taking advantage of its properties, specifically, the superior shape precision due to the low rate of volume shrinkage upon curing with light, and the ability to produce formed products, three-dimensional shaped articles, or other shaped articles having superior flexibility and mechanical characteristics. For example, a resin composition for stereolithography of the present invention can be used for stereolithographical production of a three-dimensional shaped article, and production of various formed products, for example, a film-shaped object or a molding produced by a technique such as flow casting or casting, and molds to be coated with coatings and molds used for vacuum molding.

A resin composition for stereolithography of the present invention is particularly suited for stereolithography such as above. In stereolithography applications, a resin composition for stereolithography of the present invention enables smooth production of a three-dimensional shaped article having superior toughness and mechanical characteristics while ensuring superior shape precision with a maintained low rate of volume shrinkage at the time of curing with light.

Another embodiment of the present invention is a method for producing a three-dimensional shaped article by a conventionally known stereolithography method (for example, bottom-up vat stereolithography) using any of the resin compositions for stereolithography described above.

In stereolithography using a resin composition for stereolithography of the present invention, any known stereolithography method (for example, bottom-up vat stereolithography) and device (for example, a stereolithography device such as the DIGITALWAX® 028J-Plus manufactured by DWS) may be used. In the present invention, the light energy used to cure the resin is preferably an active energy beam. As used herein, "active energy beam" means an energy ray capable of curing a resin composition for stereolithography, and includes, for example, ultraviolet light, an electron beam, X-rays, radiant rays, and high-frequency waves. For example, the active energy beam may be ultraviolet light of 300 to 400 nm wavelengths. The light source of active energy beam may be, for example, a laser such as an Ar laser or a He—Cd laser; or a lighting such as a halogen lamp, a xenon lamp, a metal halide lamp, an LED, a mercury lamp, or a fluorescent lamp. Lasers are particularly preferred. When the light source is a laser, the fabrication time can be reduced by increasing the energy level, and a three-dimensional shaped article of high shape precision can be obtained by taking advantage of the desirable convergence of a laser beam.

Stereolithography using a resin composition for stereolithography of the present invention may use any known method (for example, bottom-up vat stereolithography) and any known stereolithography system, and the method and device are not particularly limited, as noted above. However, a typical example of a stereolithography method preferred for use in the present invention is a method that produces a three-dimensional shaped article of the desired shape through a repeated procedure that includes a step of forming a cured layer by selectively applying an active energy beam to the resin composition for stereolithography so as to obtain a cured layer having a desired pattern, and a step of continuously forming another cured layer on the previously formed cured layer by similarly applying an active energy beam to a newly supplied, uncured liquid of the resin composition for stereolithography. The resulting three-dimensional shaped article may be used as it is, or may be used after improving mechanical characteristics, shape stability, or other properties by, for example, post-curing the product under applied light or heat.

A three-dimensional shaped article obtained by stereolithography is not limited to a particular structure, shape, or size, and these may be decided according to use. Typical examples of areas to which the stereolithography method of the present invention is applicable include production of various models and molds, including, for example, models for assessing external designs in a designing process; models for checking functions of components and parts; resin molds for making molds; base models for making dies; and direct molds for prototype dies. More specifically, the stereolithography method of the present invention is applicable to, for example, production of models or work models for precision components and parts, electrical and electronic components, furniture, architectural structures, automobile parts, various containers and vessels, castings, dies, and matrices. By taking advantage of the excellent strength and toughness of a shaped article of the resin composition for stereolithography, the stereolithography method of the present invention can be very effectively used for, for example, complex-shape cushioning materials in structures (for example, architectural structures), and molds for vacuum molding.

EXAMPLES

The following describes the present invention in greater detail by way of Examples. It should be noted, however, that the present invention is in no way limited by the following Examples, and various changes may be made by a person with ordinary skill in the art within the technical idea of the present invention.

The components used for the resin compositions for stereolithography according to Examples and Comparative Examples are presented below, along with the abbreviations used.

Urethanized (Meth)Acrylic Compound (A)

UDMA: 2,2,4-Trimethylhexamethylene bis(2-carbamoyloxyethyl)dimethacrylate (manufactured by Kyoeisha Chemical Co., Ltd.; molecular weight: 471)

U4TH: N,N'-(2,2,4-Trimethylhexamethylene) bis[2-(aminocarboxy)propane-1,3-diol]tetramethacrylate (manufactured by Kyoeisha Chemical Co., Ltd.; molecular weight: 673)

(Meth)Acrylate Compound (B) Containing no Urethane Bond

POBA: m-Phenoxybenzyl acrylate (manufactured by Kyoeisha Chemical Co., Ltd.)

EPPA: Ethoxylated-o-phenylphenol acrylate (manufactured by Shin-Nakamura Chemical Co., Ltd.)

Photopolymerization Initiator (C)

TPO: 2,4,6-Trimethylbenzoyldiphenylphosphine oxide

BAPO: Bis(2,4,6-trimethylbenzoyl)phenylphosphine oxide

Polymerization Inhibitor (D)

BHT 3,5-Di-t-butyl-4-hydroxytoluene

Synthesis Example 1

Production of Urethanized (Meth)Acrylic Compound (A-1)-a Having Polymer Structure (1) First, 500 g of 2,4-tolylene diisocyanate and 0.2 g of di-n-butyltin dilaurate were added into a 5 L four-neck flask equipped with a stirrer, a thermostat, a thermometer, and a condenser, and the mixture was heated to 70° C. while being stirred.

(2) Separately, 600 g of polyethylene glycol (PEG #200®, manufactured by NOF Corporation; weight-average molecular weight Mw: 200) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow reaction.

(3) Thereafter, a homogenous solution prepared by adding 400 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a urethanized (meth)acrylic compound (A-1)-a having a polymer structure (weight-average molecular weight: 800; 4 urethane bonds per molecule). The weight-average molecular weight was measured by GPC. Here, "weight-average molecular weight" means a weight-average molecular weight in terms of polystyrene.

Reference Example 1

Production of Urethanized (Meth)Acrylic Compound 1

(1) First, 250 g of isophorone diisocyanate and 0.15 g of di-n-butyltin dilaurate were added into a 5 L four-neck flask equipped with a stirrer, a thermostat, a thermometer, and a condenser, and the mixture was heated to 70° C. while being stirred.

(2) Separately, 500 g of polycarbonate polyol (Kuraray Polyol® C-1090, manufactured by Kuraray Co., Ltd.; a polymer of 1,6-hexanediol/3-methyl-1,5-pentanediol=9/1 (mass ratio); weight-average molecular weight: 1,000) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow reaction.

(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a urethanized (meth)acrylic compound 1 (weight-average molecular weight: 1,500; 4 urethane bonds per molecule). The weight-average molecular weight was measured by GPC. Here, "weight-average molecular weight" means a weight-average molecular weight in terms of polystyrene.

Measurement of Weight-Average Molecular Weight

The weight-average molecular weights of urethanized (meth)acrylic compound (A-1)-a and urethanized (meth) acrylic compound 1 were determined by GPC measurement. Tetrahydrofuran was used as eluent, and a column was prepared by joining two TSKgel SuperMultipore HZM-M columns (manufactured by Tosoh Corporation) and one TSKgel Super HZ 4000 column (manufactured by Tosoh Corporation), end to end. A GPC system HLC-8320 GPC (manufactured by Tosoh Corporation) equipped with a differential refractive index detector (RI detector) was used as GPC device. For measurement, 4 mg of a specimen was dissolved in 5 mL of tetrahydrofuran to prepare a sample solution. With the column oven temperature set to 40° C., 204 of the sample solution was injected at an eluent flow rate of 0.35 mL/min, and the resulting chromatogram of the specimen was analyzed. Separately, a standard curve relating retention time and molecular weight was created by GPC using ten polystyrene standards having a molecular weight in the 400 to 5,000,000 range. The weight-average molecular weight of the specimen was then determined from its chromatogram, using the standard curve (n=1).

Examples 1 to 9 and Comparative Examples 1 and 2

The components were mixed at an ordinary temperature (20° C.±15° C.; JIS (Japanese Industrial Standards) Z 8703: 1983) in the amounts shown in Tables 1 and 2 to prepare pastes representing resin compositions for stereolithography according to Examples 1 to 9 and Comparative Examples 1 and 2.

The resin composition for stereolithography was fabricated into a specimen of the dimensions (64.0 mm in length, 10.0 mm in width, and 3.3 mm in thickness) described in JIS T 6501:2012 (Acrylic Denture Base Resins), using a stereolithography device (DIGITALWAX® 020D, manufactured by DWS).

Strength (Flexural Modulus, Flexural Strength) and Toughness (Displacement of Flexural Fracture Point)

For cured products of the resin compositions for stereolithography according to Examples and Comparative Examples, the specimen was stored in air for 1 day, and was subjected to a three-point flexural test for evaluation. The results were taken as initial values. Specifically, a three-point flexural test was conducted for each specimen at a span length of 50 mm and a crosshead speed of 5 mm/min, using a universal testing machine (Autograph AG-I, 100 kN, manufactured by Shimadzu Corporation) (n=5). Tables 1 and 2 show mean values of the measured values. The preferred range of flexural modulus for specimens is 2.1 to 4.0 GPa, more preferably 2.5 to 3.5 GPa, even more preferably 2.75 to 3.25 GPa. The preferred flexural strength is 80 MPa or more, more preferably 90 MPa or more, even more preferably 100 MPa or more, particularly preferably 120 MPa or more. As for the displacement of fracture point, it is desirable to have no fracture. In the evaluation of displacement of fracture point, the toughness was determined as being desirable (Satisfactory) when a fracture occurred with a displacement of 10 mm or more, moderate (Acceptable) when a fracture occurred with a displacement of more than 5 mm and less than 10 mm, and poor (Unsatisfactory) when a fracture occurred with a displacement of 5 mm or less. The specimens were determined as having passed the test when the result was Acceptable or Satisfactory.

Water Resistance

The resin composition according to each Example and Comparative Example was fabricated into a cured product in the same manner as for the cured product fabricated for the measurement of toughness. The cured product was immersed in 37° C. water for 168 hours, and was measured for flexural strength in the same manner as in the flexural strength test above (n=5). Tables 1 and 2 show means values of the measured values. Water resistance is desirable when the rate of change (percentage decrease) of flexural strength is 5% or less, and even more desirable when the rate of change is 2% or less. Here, the rate of change is a percentage decrease calculated after 168 hours in 37° C. water relative to the initial flexural strength taken from the result of the flexural strength measurement conducted for the evaluation of toughness.

Rate of change (percentage decrease) of flexural strength (%)=[{initial flexural strength (MPa)−flexural strength after 168 hours in 37° C. water (MPa)}/initial flexural strength (MPa)]×100

Hardness

For cured products of the photocurable resin compositions of Examples and Comparative Examples, the flexural specimen was used to measure the hardness of the cured product at 23° C., and the measured value was used as an index of hardness. The measurement was made with a Type A durometer (Asker rubber hardness meter A Type, serial number 32330; Kobunshi Keiki Co., Ltd.) and a type D durometer (Asker rubber hardness meter D Type, serial number 35318; Kobunshi Keiki Co., Ltd.) according to JIS K 7215:1986. The results for Examples and Comparative Examples are presented in Table 1 and Table 2, respectively. In the measurement, the cured product can be said as having moderate hardness against biting, and being suitable as a denture base material, a dental occlusal splint, or an appliance for the treatment of sleep apnea when the A hardness at 23° C. is 86 or more, or when the D hardness at 23° C. is 40 to 95.

TABLE 1

| | | | Example | | | | | | | | |
|---|---|---|---|---|---|---|---|---|---|---|---|
| | | | 1 | 2 | 3 | 4 | 5 | 6 | 7 | 8 | 9 |
| Components (parts by mass) | (A) | UDMA | 65 | 50 | 80 | | 65 | 45 | | 65 | 65 |
| | | U4TH | | | | 65 | | 20 | | | |
| | | (A-1)-a | | | | | | | 65 | | |
| | (B) | POBA | 35 | 50 | 20 | 35 | | 20 | 35 | 35 | 35 |
| | | EPPA | | | | | 35 | 15 | | | |
| | (C) | TPO | 3.0 | 3.0 | 3.0 | 3.0 | 3.0 | 4.0 | 3.0 | 1.5 | 2.5 |
| | | BAPO | | 0.5 | | | | | | | |
| | (D) | BHT | 0.05 | 0.05 | 0.05 | 0.05 | 0.05 | 0.5 | 0.05 | 0.5 | 0.5 |
| Strength | | Flexural modulus (GPa) | 3.0 | 2.8 | 3.2 | 3.4 | 3.1 | 2.8 | 2.3 | 3.1 | 3.2 |
| | | Flexural strength (MPa) | 115 | 102 | 118 | 122 | 112 | 116 | 91 | 135 | 138 |
| Toughness | | Displacement of fracture point | Satisfactory | Satisfactory | Satisfactory | Acceptable | Satisfactory | Satisfactory | Satisfactory | Satisfactory | Satisfactory |
| Water resistance | | Flexural strength after immersion (MPa) | 114 | 100 | 116 | 119 | 110 | 114 | 87 | 133 | 136 |

TABLE 1-continued

| | | Example | | | | | | | | |
|---|---|---|---|---|---|---|---|---|---|---|
| | | 1 | 2 | 3 | 4 | 5 | 6 | 7 | 8 | 9 |
| | Percentage decrease (%) | 0.86 | 1.9 | 1.7 | 2.4 | 1.8 | 1.7 | 4.4 | 1.5 | 1.5 |
| Hardness | A Hardness | 92 | 90 | 93 | 95 or higher | 93 | 95 or higher | 88 | 95 or higher | 95 or higher |
| | D Hardness | 48 | 45 | 49 | 56 | 48 | 53 | 42 | 60 | 62 |

TABLE 2

| | | | Comparative Example | |
|---|---|---|---|---|
| | | | 1 | 2 |
| Components (parts by mass) | (A) | UDMA | | 65 |
| | | U4TH | | |
| | (B) | POBA | 35 | |
| | | EPPA | | |
| | (C) | TPO | 3.0 | 3.0 |
| | | BAPO | | |
| | | Urethanized (meth)acrylic compound 1 | 65 | |
| | | TEGDMA | | 35 |
| | (D) | BHT | 0.05 | 0.05 |
| Strength | | Flexural modulus (GPa) | 1.2 | 3.5 |
| | | Flexural strength (MPa) | 48 | 118 |
| Toughness | | Displacement of fracture point | Satis-factory | Unsatis-factory |
| Water resistance | | Flexural strength after immersion (MPa) | 46 | 117 |
| | | percentage decrease (%) | 4.2 | 0.86 |
| Hardness | | A Hardness | 82 | 95 or higher |
| | | D Hardness | 28 | 92 |

TEGDMA: Triethylene glycol dimethacrylate (manufactured by Shin-Nakamura Chemical Co., Ltd.)

As shown in Tables 1 and 2, the shaped articles of the resin compositions for stereolithography of Examples 1 to 9 were superior in terms of strength, toughness, and water resistance. The strength of the shaped articles of the resin compositions for stereolithography of Examples 1 to 9 was particularly superior compared to the strength of the shaped article of the resin composition of Comparative Example 1. The toughness of the shaped articles of the resin compositions for stereolithography of Examples 1 to 9 was superior to the toughness of the shaped article of the resin composition of Comparative Example 2. The water resistance of the shaped articles of the resin compositions for stereolithography of Examples 1 to 9 was superior to the water resistance of the shaped article of the resin composition of Comparative Example 2.

INDUSTRIAL APPLICABILITY

A resin composition for stereolithography of the present invention excels in strength, toughness, and water resistance in the form of a shaped article. This makes a resin composition for stereolithography of the present invention suited for intraoral use as a dental material (particularly, a denture base material or a dental occlusal splint) or a material for treating sleep disorders (particularly, an appliance for the treatment of sleep apnea).

The invention claimed is:

1. A resin composition for stereolithography, comprising:

a urethanized (meth)acrylic compound (A), a (meth) acrylate compound (B) containing no urethane bond, a photopolymerization initiator (C), and 0.1 to 100 parts by mass relative to 100 parts by mass of the photopolymerization initiator (C) of a polymerization inhibitor (D), the urethanized (meth)acrylic compound (A) being a urethanized (meth)acrylic compound (A-1) having a polymer structure, the urethanized (meth)acrylic compound (A-1) having a polymer structure having a weight-average molecular weight of less than 1,000, the (meth)acrylate compound (B) containing no urethane bond comprising at least one selected from the group consisting of a (meth)acrylate compound (b-I) represented by the following general formula (I), and a (meth)acrylate compound (b-II) represented by the following general formula (II):

(I)

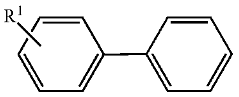

(II)

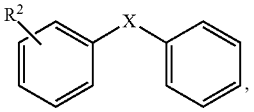, wherein $R^1$ and $R^2$ are each independently a group represented by the following general formula (i), or a group represented by the following general formula (ii), and X is a C1 to C6 divalent hydrocarbon group, or an oxygen atom, (i)

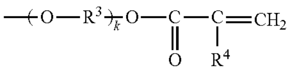

(ii)

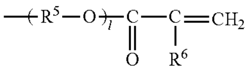

wherein $R^3$ and $R^5$ are each independently a C1 to C10 divalent hydrocarbon group, $R^4$ and $R^6$ are each independently a hydrogen atom or a methyl group, and k and l are each independently an integer of 0 to 6, and wherein said resin composition for stereolithography further comprises a urethanized (meth)acrylic compound (A-2) having no polymer structure comprising 2,2,4-trimethylhexamethylene bis(2-carbamoyloxyethyl)dimethacrylate and/or N,N'-(2,2,4-trimethylhexamethylene)bis[2-(aminocarboxy)propane-1,3-diol]tetramethacrylate.

2. The resin composition for stereolithography according to claim 1, wherein the number of the urethane bonds is three or fewer per molecule in the urethanized (meth)acrylic compound (A-1) having a polymer structure.

3. The resin composition for stereolithography according to claim 1, wherein the urethanized (meth)acrylic compound (A-1) having a polymer structure is a (meth)acrylate compound.

4. The resin composition for stereolithography according to claim 1, wherein the content of the urethanized (meth) acrylic compound (A-1) having a polymer structure is in the range of 51 to 95 mass % in 100 mass % of polymerizable compounds.

5. The resin composition for stereolithography according to claim 1, wherein the polymer structure is a structure selected from the group consisting of a polyester, a polycarbonate, a polyurethane, a polyether, a poly-conjugated diene, and a hydrogenated poly-conjugated diene.

6. The resin composition for stereolithography according to claim 1, wherein k and l are each independently an integer of 1 to 4.

7. The resin composition for stereolithography according to claim 1, wherein the (meth)acrylate compound (B) containing no urethane bond comprises the (meth)acrylate compound (b-II), and X is an oxygen atom.

8. The resin composition for stereolithography according to claim 7, wherein $R^2$ is a group represented by the general formula (ii).

9. The resin composition for stereolithography according to claim 1, wherein the (meth)acrylate compound (B) containing no urethane bond comprises the (meth)acrylate compound (b-I), and $R^1$ is a group represented by the general formula (i).

10. The resin composition for stereolithography according to claim 1, wherein the content of the photopolymerization initiator (C) is in the range of 0.01 to 20 parts by mass relative to total 100 parts by mass of the urethanized (meth)acrylic compound (A) and the (meth)acrylate compound (B) containing no urethane bond.

11. The resin composition for stereolithography according to claim 1, wherein a cured product of the resin composition for stereolithography has a flexural strength of 100 MPa or more, and a flexural modulus of 2.1 GPa or more.

12. A dental material, comprising:
a shaped article of the resin composition for stereolithography according to claim 1.

13. A denture base material, comprising:
a shaped article of the resin composition for stereolithography according to claim 1.

14. A dental occlusal splint, comprising:
a shaped article of the resin composition for stereolithography according to claim 1.

15. A material for treating sleep disorder, comprising:
a shaped article of the resin composition for stereolithography according to claim 1.

16. A method, comprising:
stereolithographically producing a three-dimensional shaped article with the resin composition for stereolithography according to claim 1.

* * * * *